US010031070B2

(12) United States Patent
Chiba

(10) Patent No.: US 10,031,070 B2
(45) Date of Patent: Jul. 24, 2018

(54) ANALYZING DEVICE AND ANALYZING METHOD BASED ON IMAGES OF BIOLOGICAL TISSUE CAPTURED UNDER ILLUMINATION OF LIGHT WITH DIFFERENT ILLUMINATION WAVELENGTH RANGES

(71) Applicant: HOYA CORPORATION, Tokyo (JP)

(72) Inventor: Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 303 days.

(21) Appl. No.: 14/936,965

(22) Filed: Nov. 10, 2015

(65) Prior Publication Data
US 2016/0146723 A1 May 26, 2016

(30) Foreign Application Priority Data

Nov. 21, 2014 (JP) .................. 2014-236471

(51) Int. Cl.
*G01N 21/25* (2006.01)
*G01N 33/483* (2006.01)
(Continued)

(52) U.S. Cl.
CPC ......... *G01N 21/25* (2013.01); *A61B 1/00009* (2013.01); *A61B 1/00186* (2013.01);
(Continued)

(58) Field of Classification Search
CPC ............... G01N 21/25; G01N 33/4833; G01N 2021/1765; A61B 5/1459; A61B 5/14551;
(Continued)

(56) References Cited

U.S. PATENT DOCUMENTS 7,892,169 B2 2/2011 Gono et al.
7,949,387 B2 5/2011 Khoobehi et al.
(Continued)

FOREIGN PATENT DOCUMENTS

CN 103070658 5/2013
CN 103654687 3/2014
(Continued)

OTHER PUBLICATIONS

US 9,560,957, 02/2017, Yokouchi et al. (withdrawn)
(Continued)

*Primary Examiner* — Que T Le
*Assistant Examiner* — Jennifer Bennett
(74) *Attorney, Agent, or Firm* — Greenblum & Bernstein, P.L.C.

(57) ABSTRACT

An analyzing device, comprising: a light source device; an image pick-up device that generates image data by capturing a biological tissue illuminated with light emitted by the light source device; and an index calculation unit configured to calculate an index representing a molar ratio between first and second biological substances contained in the biological tissue based on the image data, wherein: the light source device switches between light of a first illumination wavelength range which the first and second biological substances absorb and light of a second illumination wavelength range lying within the first illumination wavelength range; and the index calculation unit calculates the index based on first image data obtained by capturing the biological tissue under illumination of the light of the first illumination wavelength range and second image data obtained by capturing the biological tissue under illumination of the light of the second illumination wavelength range.

23 Claims, 6 Drawing Sheets

(51) Int. Cl.
  *A61B 5/1459* (2006.01)
  *A61B 5/1455* (2006.01)
  *A61B 1/00* (2006.01)
  *G06T 7/00* (2017.01)
  *A61B 1/06* (2006.01)
  *A61B 5/00* (2006.01)
  *G01N 21/17* (2006.01)

(52) U.S. Cl.
  CPC .......... *A61B 1/0638* (2013.01); *A61B 1/0646* (2013.01); *A61B 5/1459* (2013.01); *A61B 5/14551* (2013.01); *G01N 33/4833* (2013.01); *G06T 7/0012* (2013.01); *A61B 5/0075* (2013.01); *G01N 2021/1765* (2013.01); *G06T 2207/10016* (2013.01); *G06T 2207/10024* (2013.01); *G06T 2207/10068* (2013.01); *G06T 2207/10152* (2013.01); *G06T 2207/30096* (2013.01)

(58) Field of Classification Search
  CPC . A61B 1/00009; A61B 1/0646; A61B 1/0638; A61B 1/00186; A61B 5/0075; G06T 7/0012; G06T 2207/30096; G06T 2207/10068; G06T 2207/10024; G06T 2207/10016; G06T 2207/10152
  See application file for complete search history.

(56) References Cited

U.S. PATENT DOCUMENTS

| | | | |
|---|---|---|---|
| 8,681,208 | B2 | 3/2014 | Yoshino |
| 8,913,111 | B2 | 12/2014 | Takahashi |
| 9,277,190 | B2 | 3/2016 | Igarashi et al. |
| 9,370,297 | B2 | 6/2016 | Yokouchi et al. |
| 9,414,741 | B2 | 8/2016 | Yamamoto |
| 9,591,966 | B2 | 3/2017 | Yokouchi et al. |
| 2003/0158470 | A1 | 8/2003 | Wolters et al. |
| 2003/0176768 | A1* | 9/2003 | Gono ............... A61B 1/0638 600/109 |
| 2005/0027166 | A1 | 2/2005 | Matsumoto et al. |
| 2009/0069653 | A1* | 3/2009 | Yoshida ............ A61B 5/0073 600/323 |
| 2009/0137908 | A1 | 5/2009 | Patwardhan |
| 2010/0168584 | A1 | 7/2010 | Fujinuma et al. |
| 2011/0230715 | A1 | 9/2011 | Saito |
| 2011/0237915 | A1 | 9/2011 | Yamaguchi |
| 2011/0254937 | A1 | 10/2011 | Yoshino |
| 2012/0116159 | A1 | 5/2012 | Mizuyoshi et al. |
| 2012/0116192 | A1* | 5/2012 | Saito ............... A61B 1/00009 600/323 |
| 2012/0157768 | A1 | 6/2012 | Saito |
| 2012/0215066 | A1 | 8/2012 | Akiyama et al. |
| 2012/0302847 | A1 | 11/2012 | Ozawa et al. |
| 2012/0327205 | A1 | 12/2012 | Takahashi |
| 2013/0039147 | A1 | 2/2013 | Witte et al. |
| 2013/0162790 | A1 | 6/2013 | Tanaka et al. |
| 2013/0245419 | A1 | 9/2013 | Oishi |
| 2013/0289373 | A1 | 10/2013 | Yamamoto |
| 2013/0310668 | A1 | 11/2013 | Young |
| 2013/0345517 | A1 | 12/2013 | Morimoto et al. |
| 2014/0066733 | A1* | 3/2014 | Saito ............... A61B 5/14542 600/339 |
| 2014/0152790 | A1 | 6/2014 | Saito et al. |
| 2014/0185907 | A1* | 7/2014 | Chiba ............... A61B 1/00009 382/134 |
| 2014/0235973 | A1* | 8/2014 | Brittenham ........ A61B 5/0071 600/317 |
| 2016/0120449 | A1 | 5/2016 | Chiba |

FOREIGN PATENT DOCUMENTS

| | | |
|---|---|---|
| CN | 103654690 | 3/2014 |
| CN | 103796566 | 5/2014 |
| CN | 105324064 | 2/2016 |
| EP | 2449950 | 5/2012 |
| EP | 2468187 | 6/2012 |
| EP | 2689712 | 1/2014 |
| EP | 2702938 | 3/2014 |
| EP | 3005933 | 4/2016 |
| JP | 6-79594 | 10/1994 |
| JP | 2002-95635 | 4/2002 |
| JP | 3559755 | 9/2004 |
| JP | 3583731 | 11/2004 |
| JP | 3607857 | 1/2005 |
| JP | 2007-29453 | 2/2007 |
| JP | 2011-10998 | 1/2011 |
| JP | 2011-224038 | 11/2011 |
| JP | 2012-100800 | 5/2012 |
| JP | 2012-235962 | 12/2012 |
| JP | 2012-245223 | 12/2012 |
| JP | 2013-39215 | 2/2013 |
| JP | 2013-63097 | 4/2013 |
| JP | WO 2013047054 A1 * | 4/2013 ......... A61B 1/00009 |
| JP | 5362149 | 12/2013 |
| JP | 2014-230647 | 12/2014 |
| JP | 2014-233344 | 12/2014 |
| WO | 2011/080996 | 7/2011 |
| WO | 2011/099322 | 8/2011 |
| WO | 2011/162111 | 12/2011 |
| WO | 2012/047806 | 4/2012 |
| WO | 2012/090552 | 7/2012 |
| WO | 2013/047054 | 4/2013 |
| WO | 2014/192781 | 12/2014 |

OTHER PUBLICATIONS

Extended European Search Report issued in European Patent Appl. No. 16175262.1, dated Nov. 17, 2016.
U.S. Appl. No. 15/295,048 to Fumika Yokouchi et al., filed Oct. 17, 2016.
International Search Reporting (ISR) in International Application PCT/JP2016/058112, dated Jun. 7, 2016.
Office Action in U.S. Appl. No. 15/295,048, dated Nov. 22, 2016.
U.S. Appl. No. 15/308,479 to Fumika Yokouchi, filed Nov. 2, 2016.
Office Action issued in European Patent Appl. No. 15183306.8, dated Jan. 24, 2017.
Extended European Search Report issued in European Patent Appl. No. 14805121.2, dated Mar. 20, 2017.
Office Action issued in Japan Patent Appl. No. 2014-179036, dated Feb. 23, 2017.
Office Action issued in U.S. Appl. No. 15/295,048, dated Apr. 12, 2017.
Office Action issued in China Patent Appl. No. 201510549104.2, dated Apr. 18, 2017, along with an english translation thereof.
European Search Report issued in European Patent Application No. 15195635.6, dated Apr. 18, 2016.
European Search Report issued in European Patent Application No. 15183306.8, dated Feb. 5, 2016.
U.S. Appl. No. 14/894,119 to Toru Chiba, filed Nov. 25, 2015.
U.S. Appl. No. 14/837,300 to Toru Chiba, filed Aug. 27, 2015.
Office Action issued in Japan Patent Appl. No. 2012-180902, dated May 24, 2016, along with an English translation thereof.
Office Action issued in China Patent Appl. No. 201310358808.2, dated Jun. 24, 2016, along with an English translation thereof.
Office Action issued in China Patent Appl. No. 201310358808.2, dated Nov. 4, 2015, along with an English translation thereof.
Office Action issued in Japan Patent Appl. No. 2012-180902, dated Dec. 26, 2016, along with an English translation thereof.
Office Action issued in China Patent Appl. No. 201310358808.2, dated Jan. 16, 2017, along with an English translation thereof.
Office Action issued in U.S. Appl. No. 14/837,300, dated Apr. 13, 2018.

* cited by examiner

ANALYZING DEVICE AND ANALYZING METHOD BASED ON IMAGES OF BIOLOGICAL TISSUE CAPTURED UNDER ILLUMINATION OF LIGHT WITH DIFFERENT ILLUMINATION WAVELENGTH RANGES

BACKGROUND OF THE INVENTION

The present invention relates to an analyzing device and an analyzing method for obtaining an index indicating concentration of biological substances in a biological tissue.

Recently, an endoscope device having a function of photographing spectroscopic image (spectral endoscope device) has been proposed. By using such a spectral endoscope device, it is possible to obtain information concerning spectral property (e.g., reflection spectrum) of a biological tissue such as a mucous membrane of a digestive organ. It is known that the reflection spectrum of a biological tissue reflects information concerning types or densities of components contained in the vicinity of a surface layer of a biological tissue being a measurement target. Specifically, it is known that an absorbance calculated from the reflection spectrum of a biological tissue equals to an absorbance obtained by linearly superimposing absorbances of a plurality of substances that compose the biological tissue.

It is known that composition and amount of substances in a lesion biological tissue differ from those in a healthy biological tissue. It is reported in many of the earlier studies that abnormalities of lesions represented by such as cancer are particularly deeply related to a condition of blood, especially to an overall amount of blood or oxygen saturation. Qualifying and quantifying two focused biological tissues by using spectroscopic feature values within the visible range that the two focused biological tissues have is a frequently used method in the field of spectrographic analysis. Therefore, it is possible to estimate existence of some kind of lesions in a biological tissue by comparing a spectral characteristic of blood in a biological tissue that includes lesions with a spectral characteristic of blood in a biological tissue that does not include lesions.

A spectral image is composed of a series of image information captured using light of different wavelengths, and more detailed spectral information of a biological tissue can be obtained from the spectral image having higher wavelength resolutions (i.e., larger number of wavelengths used to acquire image information). Japanese Patent Provisional Publication No. 2012-245223A (hereafter, referred to as Patent Document 1) discloses an exemplary configuration of a spectral endoscope device which acquires spectral images in a wavelength range of 400-800 nm at 5 nm intervals.

SUMMARY OF THE INVENTION

However, in order to acquire spectral images having high wavelength resolutions, such as the spectral images disclosed in Patent Document 1, lots of images need to be captured while changing an image pick-up wavelength. Furthermore, a large amount of calculation is necessary to analyze lots of images and thus it takes time to analyze them. That is, relatively complicated photographing operations and calculations need to be repeated to obtain effective diagnosis support information. Accordingly, there is a problem that it takes time to obtain the effective diagnosis support information.

The present invention is made in view of the above situation. That is, the object of the present invention is to provide an analyzing device and an analyzing method capable of acquiring image information showing distributions of biological substances, such as oxygen saturation distribution, in a short time.

According to an aspect of the invention, there is provided an analyzing device, comprising: a light source device; an image pick-up device that generates image data by capturing a biological tissue illuminated with light emitted by the light source device; and an index calculation unit configured to calculate an index X representing a molar ratio between a first biological substance and a second biological substance contained in the biological tissue based on the image data. In this configuration, the light source device switches between light of a first illumination wavelength range which the first biological substance and the second biological substance absorb and light of a second illumination wavelength range lying within the first illumination wavelength range. The index calculation unit is configured to calculate the index X based on first image data $G_1$ obtained by capturing the biological tissue under illumination of the light of the first illumination wavelength range and second image data $G_2$ obtained by capturing the biological tissue under illumination of the light of the second illumination wavelength range.

With this configuration, it becomes possible to obtain image information representing distribution of biological substances, such as oxygen saturation, in a short time.

In at least one aspect, the first illumination wavelength range may include both of an absorption peak wavelength of the first biological substance and an absorption peak wavelength of the second biological substance, and the second illumination wavelength range may include an absorption peak wavelength of one of the first biological substance and the second biological substance.

In at least one aspect, the first illumination wavelength range may include: a shorter wavelength side range which is situated to adjoin a shorter wavelength side edge of the second illumination wavelength range and includes an absorption peak of the other of the first biological substance and the second biological substance; and a longer wavelength side range which is situated to adjoin a longer wavelength side edge of the second illumination wavelength range and includes an absorption peak of the other of the first biological substance and the second biological substance.

In at least one aspect, the light source device may comprise: a light source that emits wide band light; a first optical filter that selectively extracts the light of the first illumination wavelength range from the wide band light; and a second optical filter that selectively extracts the light of the second illumination wavelength range from the wide band light.

In at least one aspect, the index calculation unit may operate to: calculate an absorption $A_1$ of the biological tissue in the first illumination wavelength range based on the first image data $G_1$; calculate an absorption $A_2$ of the biological tissue in the second illumination wavelength range based on the second image data $G_2$; and calculate the index X based on the absorption $A_1$ and the absorption $A_2$.

In at least one aspect, the index calculation unit may calculate the absorption $A_1$ by one of following expressions (1) and (2):

$$A_1 = -\log G_1 \qquad (1)$$

$$A_1 = -G_1 \qquad (2).$$

The index calculation unit may calculate the absorption $A_2$ by one of following expressions (3) and (4):

$$A_2 = -\log G_2 \tag{3}$$

$$A_2 = -G_2 \tag{4}$$

In at least one aspect, the index calculation unit may calculate the index X by one of following expressions (5) and (6):

$$X = A_1 - 2kA_2 \tag{5}$$

$$X = A_1 - 3kA_2 \tag{6}$$

where k is a constant number.

In at least one aspect, the index calculation unit may calculate the index X by a following expression (7):

$$X = w1 \cdot A_1 - k \cdot (w1 + w2) \cdot A_2 \tag{7}$$

where k, w1 and w2 are constant numbers

In at least one aspect, the index calculation unit may calculate the index X by a following expression (8):

$$X = \frac{w1}{w2} \cdot \left(\frac{A_1}{kA_2} - 1\right) \tag{8}$$

where k, w1 and w2 are constant numbers.

In at least one aspect, the index calculation unit may calculate the index X by a following expression (9):

$$X = \frac{(A_1 - kA_2)^{w1}}{(kA_2)^{w2}} \tag{9}$$

where k, w1 and w2 are constant numbers.

In at least one aspect, the constant number k may be determined such that a value of the index X calculated based on the first image data $G_1$ and the second image data $G_2$ obtained by capturing a biological tissue whose molar ratio is known becomes closest to a theoretical value of the index X.

In at least one aspect, by obtaining measurement values of the indexes X of a plurality of different biological tissues whose molar ratios are known, the constant number k may be determined such that a calibration curve representing a relationship between the known molar ratios and the measurement values of the indexes becomes closest to a reference line representing a relationship between the known molar ratios and theoretical values of the indexes X.

In at least one aspect, the constant number k may be 1.

In at least one aspect, the light source device may comprise a third optical filter that selectively extracts, from the wide band light, light of a third illumination wavelength range in which a degree of absorption by the biological tissue is sufficiently lower than that in the first illumination wavelength range. In this case, the image pick-up device may generate third image data $R_3$ by capturing the biological tissue under illumination of the light of the third illumination wavelength range. The index calculation unit may be configured to calculate a first standardized reflectivity $SR_1$ by dividing the first image data $G_1$ by the third image data $R_3$ and to calculate the absorption $A_1$ by one of following expressions (10) and (11):

$$A_1 = -\log SR_1 \tag{10}$$

$$A_1 = -SR_1 \tag{11}$$

The index calculation unit may be configured to calculate a second standardized reflectivity $SR_2$ by dividing the second image data $G_2$ by the third image data $R_3$ and to calculate the absorption $A_2$ by one of following expressions (12) and (13):

$$A_2 = -\log SR_2 \tag{12}$$

$$A_2 = -SR_2 \tag{13}$$

In at least one aspect, the image pick-up device may obtain first baseline image data $BL_1$ by capturing a colorless reference board under illumination of the light of the first illumination wavelength range, second baseline image data $BL_2$ by capturing the colorless reference board under illumination of the light of the second illumination wavelength range, and third baseline image data $BL_3$ by capturing the colorless reference board under illumination of the light of the third illumination wavelength range. In this case, the index calculation unit may be configured to calculate the first standardized reflectivity $SR_1$ by a following expression (14), and calculates the second standardized reflectivity $SR_2$ by a following expression (15):

$$SR_1 = \frac{G_1/BL_1}{R_3/BL_3} \tag{14}$$

$$SR_1 = \frac{G_2/BL_2}{R_3/BL_3}. \tag{15}$$

In at least one aspect, the image pick-up device may be a color image pick-up device having an RGB color filter. In this case, the third illumination wavelength range may be a red color wavelength range. The third image data $R_3$ may be image data obtained by a light-receiving element of the image pick-up device to which an R filter of the RGB color filter is attached.

In at least one aspect, the image pick-up device may be a color image pick-up device having an RGB color filter. In this case, the image pick-up device may obtain first baseline image data $BL_1$ by capturing a colorless reference board under illumination of the light of the first illumination wavelength band, second baseline image data $BL_2$ by capturing the colorless reference board under illumination of the light of the second illumination wavelength band, third baseline image data $BL_{3R}$, $BL_{3G}$ and $BL_{3B}$ of three primary colors by capturing the colorless reference board under illumination of the wide band light, and normal observation image data $R_N$, $G_N$ and $B_N$ of three primary colors by capturing the biological tissue under illumination of the wide band light. The index calculation unit may be configured to calculate the first standardized reflectivity $SR_1$ by a following expression (16), and calculates the second standardized reflectivity $SR_2$ by a following expression (17):

$$SR_1 = \frac{G_1/BL_1}{\frac{R_N}{BL_{3R}} + \frac{G_N}{BL_{3G}} + \frac{B_N}{BL_{3B}}} \tag{16}$$

$$SR_2 = \frac{G_2/BL_2}{\frac{R_N}{BL_{3R}} + \frac{G_N}{BL_{3G}} + \frac{B_N}{BL_{3B}}}. \tag{17}$$

In at least one aspect, the analyzing device may further comprise a light reduction unit configured to reduce the light of the first illumination wavelength range such that exposure to obtain the first image data $G_1$ becomes substantially equal to exposure to obtain the second image data $G_2$.

In at least one aspect, the first biological substance may be oxyhemoglobin, the second biological substance may be deoxyhemoglobin, and the molar ratio may be oxygen saturation.

In at least one aspect, absorption by the first biological substance and the second biological substance may correspond to a Q-band of hemoglobin. The image pick-up device may have an RGB color filter. The first image data $G_1$ and the second image data $G_2$ may be image data obtained by a light-receiving element of the image pick-up device to which a G filter of the RGB color filter is attached.

In at least one aspect, the index calculation unit may be configured to generate a distribution image representing distribution of the molar ratio between the first biological substance and the second biological substance in the biological tissue based on the index X.

In at least one aspect, the wide band light may be white light. The image pick-up device may obtain normal image data by capturing the biological tissue under illumination of the white light. The index calculation unit may be configured to: calculate an index Y representing a total hemoglobin amount based on the first image data $G_1$; extract, as a lesion portion, a pixel having the index Y larger than a first reference value and having the index X smaller than a second reference value; and generate a lesion region highlighting image in which the pixel corresponding to the lesion region of the normal observation image data is highlighted In at least one aspect, the analyzing device may further comprise an endoscope having a tip portion in which the image pick-up device is provided.

According to another aspect of the invention, there is provided an analyzing method implemented on an analyzing device, comprising: obtaining first image data $G_1$ by capturing a biological tissue under illumination of light of a first illumination wavelength range which a first biological substance and a second biological substance contained in the biological tissue absorb; obtaining second image data $G_2$ by capturing the biological tissue under illumination of light of a second illumination wavelength range lying within the first illumination wavelength range; and calculating an index X representing a molar ratio between the first biological substance and the second biological substance contained in the biological tissue based on the first image data $G_1$ and the second image data $G_2$.

With this configuration, it becomes possible to obtain image information representing distribution of biological substances, such as oxygen saturation, in a short time.

BRIEF DESCRIPTION OF THE
ACCOMPANYING DRAWINGS

FIGS. 7A and 7B show display examples of image data generated by the endoscope device, in which FIG. 7A shows two-dimensional representation of an oxygen saturation distribution image and FIG. 7B shows three-dimensional representation of the oxygen saturation distribution image.

DETAILED DESCRIPTION OF THE
EMBODIMENTS

In the following, an embodiment according to the present invention is described with reference to the accompanying drawings.

An endoscope device according to the embodiment of the present invention described below is a device that quantitatively analyzes biological information (e.g., oxygen saturation) of an object on the basis of a plurality of images captured using light of different wavelengths and displays the analysis result as images. In a quantitative analysis of the oxygen saturation described below, a characteristic that a spectral property of blood (i.e., spectral property of hemoglobin) continuously changes in accordance with the oxygen saturation is used.

(Principles for Calculation of Spectral Property of Hemoglobin and Oxygen Saturation)

Before explaining a detailed configuration of an endoscope device according to the embodiment of the present invention, principles for calculation of the spectral property of hemoglobin and the oxygen saturation used in the embodiment will be described.

Figure 1:
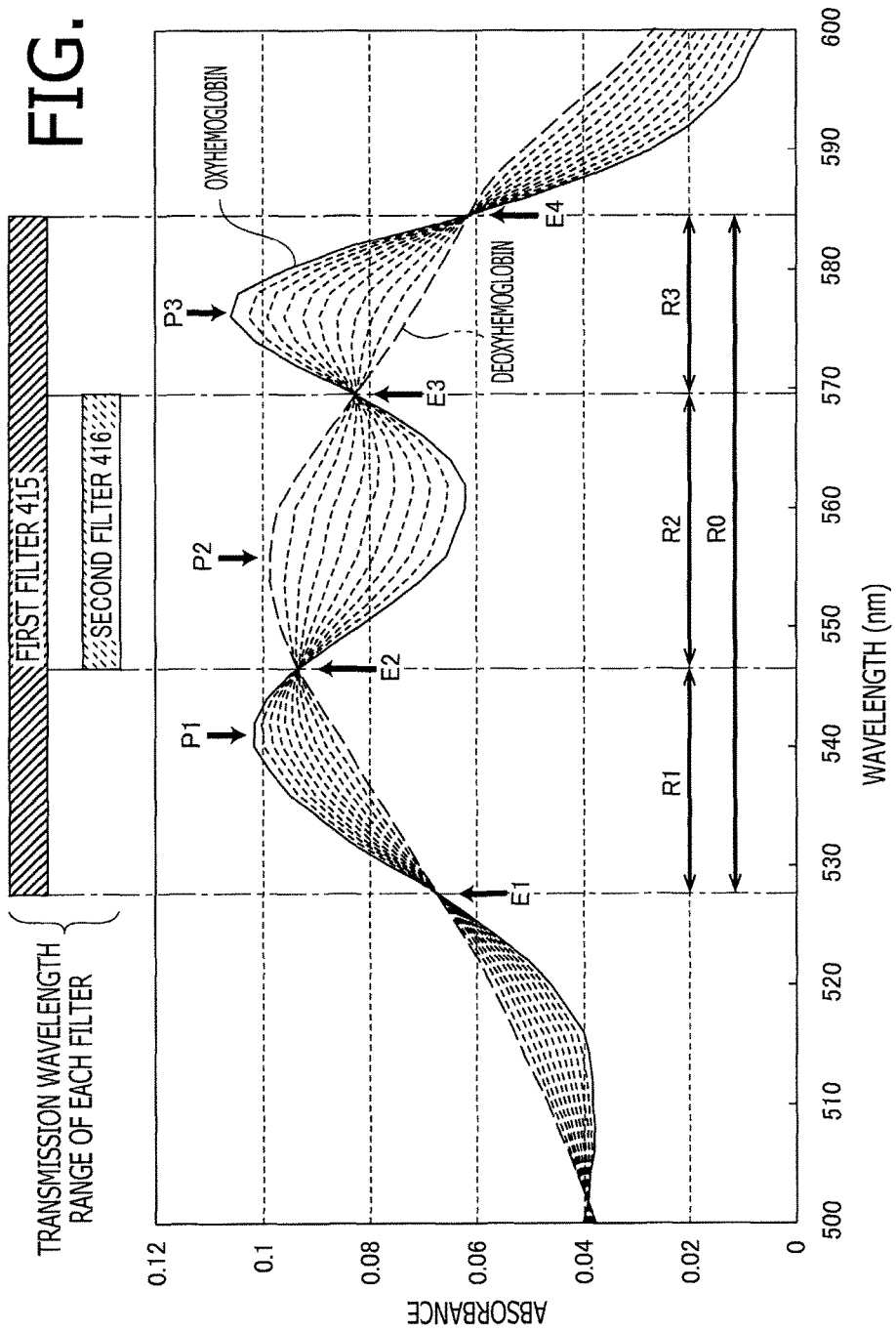
FIG. 1 shows an absorption spectrum of in Q-band of hemoglobin.

FIG. 1 shows an absorption spectrum of hemoglobin at wavelengths of around 550 nm. Hemoglobin has a strong absorption band, derived from porphyrin, called Q-band at wavelengths of around 550 nm. The absorption spectrum of hemoglobin changes in accordance with the oxygen saturation (ratio of oxyhemoglobin to the overall hemoglobin). A waveform shown in a solid line in FIG. 1 is an absorption spectrum of hemoglobin when the oxygen saturation is 100% (i.e., an absorption spectrum of oxyhemoglobin HbO), and a waveform shown in a long-dashed line is an absorption spectrum of hemoglobin when the oxygen saturation is 0% (i.e., an absorption spectrum of deoxyhemoglobin Hb). Waveforms shown in short-dashed lines are absorption spectra of hemoglobin (a mixture of oxyhemoglobin and deoxyhemoglobin) at oxygen saturations of between 0% and 100% (10, 20, 30, . . . , 90%).

As shown in FIG. 1, at Q-band, oxyhemoglobin and deoxyhemoglobin show peak wavelengths that differ from each other. Specifically, oxyhemoglobin has an absorption peak P1 at a wavelength of around 542 nm, and an absorption peak P3 at a wavelength of around 576 nm. On the other hand, deoxyhemoglobin has an absorption peak P2 at a wavelength of around 556 nm. Since FIG. 1 shows a two-component absorption spectrum in which a sum of a concentration of each component (oxyhemoglobin and deoxyhemoglobin) is constant, isosbestic points E1, E2, E3 and E4, where absorbances are constant regardless of the concentration of each component (i.e., oxygen saturation), appear. In the following description, a wavelength range between isosbestic points E1 and E2 is referred to as wavelength range R1, a wavelength range between isosbestic points E2 and E3 is referred to as wavelength range R2, and a wavelength range between isosbestic points E3 and E4 is referred to as wavelength range R3. Further, a wavelength range between isosbestic points E1 and E4 is referred to as wavelength range R0.

As shown in FIG. 1, between neighboring isosbestic points, absorbance of hemoglobin monotonically increases or decreases with the oxygen saturation. Further, between neighboring isosbestic points, absorbance of hemoglobin almost linearly changes with the oxygen saturation.

Specifically, absorbances $A_{R1}$ and $A_{R3}$ of hemoglobin at wavelength ranges R1 and R3 linearly increases with oxyhemoglobin concentration (oxygen saturation), and absorbance $A_{R2}$ of hemoglobin at wavelength range R2 linearly increases with deoxyhemoglobin concentration (1-"oxygen saturation"). Therefore, an index X, defined by the following expression (18), linearly increases with oxyhemoglobin concentration (oxygen saturation).

$$X=(A_{R1}+A_{R3})-A_{R2} \qquad (18)$$

Therefore, the oxygen saturation can be calculated from the index X by experimentally acquiring a quantitative relationship between the oxygen saturation and the index X.

(Configuration of Endoscope Device)

Figure 2:
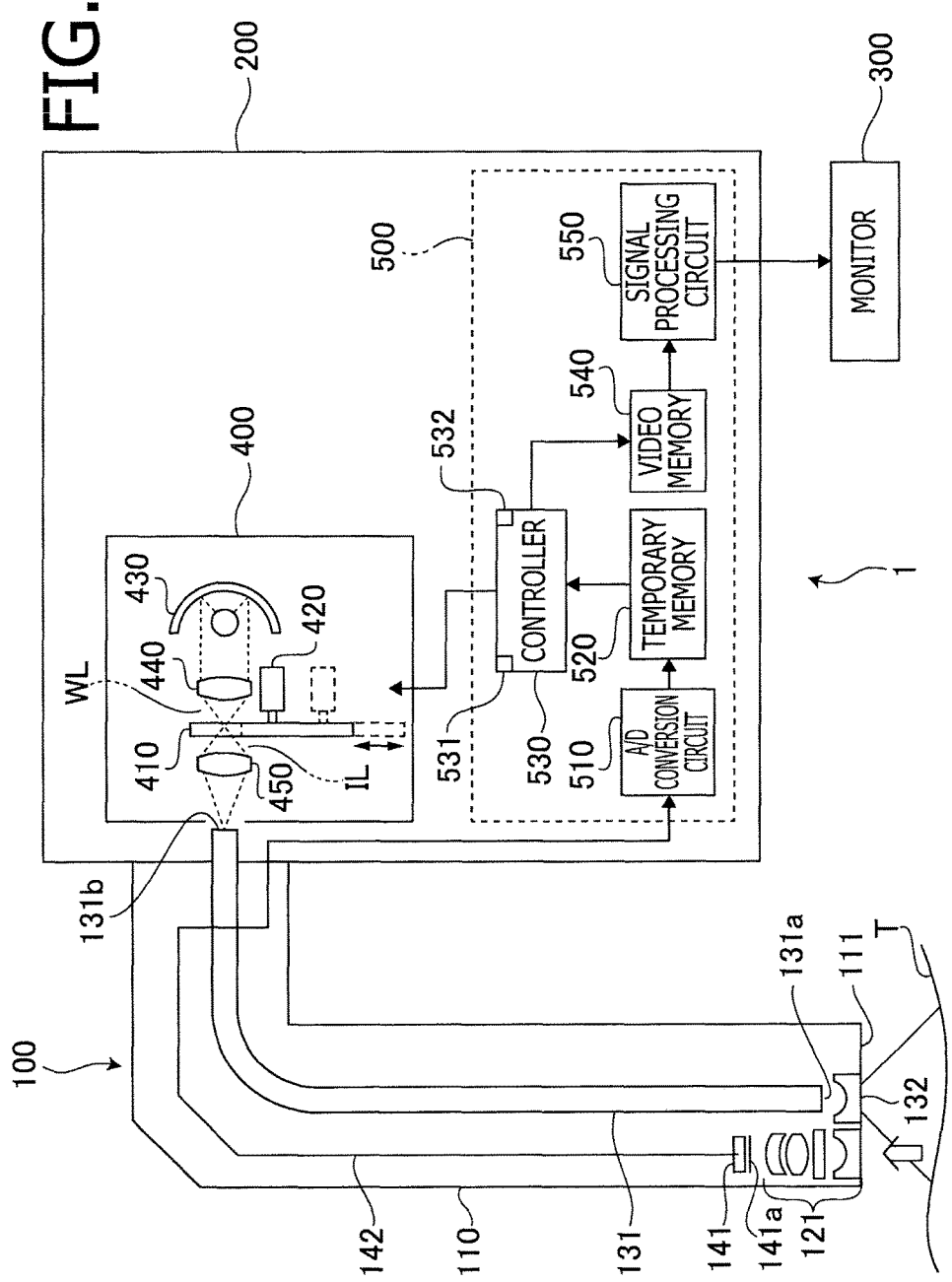
FIG. 2 is a block diagram illustrating a configuration of an endoscope device according to an embodiment of the invention.

FIG. 2 is a block chart illustrating an endoscope device 1 according to the embodiment of the present invention. The endoscope device 1 of the present embodiment comprises an electronic endoscope 100, a processor 200 and a monitor 300. The electronic endoscope and the monitor 300 are detachably connected to the processor 200. Also, the processor 200 includes therein a light source unit 400 and an image processor unit 500.

The electronic endoscope 100 has an insertion tube 110 to be inserted into a body cavity. The electronic endoscope 100 is provided with a light guide 131 which extends over the full length of the electronic endoscope 100. One end portion of the light guide 131 (tip portion 131a) is arranged close to a tip portion of the insertion tube 110 (insertion tube tip portion 111), and the other end portion of the light guide 131 (end portion 131b) is connected to the processor 200. The processor 200 includes therein the light source unit 400 comprising a light source lamp 430, e.g., a Xenon lamp which generates a large amount of white light WL. The illumination light IL generated by the light source unit 400 is incident on the end portion 131b of the light guide 131. The light which is incident on the proximal end portion 131b of the light guide 131 is guided to the tip portion 131a through the light guide 131, and is emitted from the tip portion 131a. At the insertion tube tip portion 111 of the electronic endoscope 100, a light distribution lens 132 is arranged to face the tip portion 131a of the light guide 131. The illumination light IL emitted from the tip portion 131a of the light guide 131 passes through the distribution lens 132, and illuminates the biological tissue T near the insertion tube tip portion 111.

An objective optical system 121 and an image pick-up device 141 are provided at the insertion tube tip portion 111. A portion of light which is reflected or scattered by the surface of the biological tissue T (return light) is incident on the objective optical system 121 and condensed, and forms an image on a light-receiving surface of the image pick-up device 141. The image pick-up device 141 of the present embodiment is a color image capturing CCD (Charge Coupled Device) image sensor comprising a color filter 141a on a light-receiving surface thereof, but other types of image pick-up device such as CMOS (Complementary Metal Oxide Semiconductor) image sensor may also be used. The color filter 141a is a so-called on-chip filter, in which an R filter that transmits red light, a G filter that transmits green light, and a B filter that transmits blue light are arranged, which is directly formed on each light-receiving element of the image pick-up device 141. Each of the R filter, G filter and B filter has a spectral property shown in FIG. 3. That is, the R filter of the present embodiment is a filter that transmits light having wavelengths of longer than about 570 nm, the G filter is a filter that transmits light having wavelengths of between about 470-620 nm, and the B filter is a filter that transmits light having wavelengths of shorter than about 530 nm.

The image pick-up device 141 is controlled to drive in synchronization with a signal processing circuit 550 which will be described later, and periodically (e.g., at 1/30 seconds interval) outputs imaging signals corresponding to an image formed on the light-receiving surface. The imaging signals which are outputted from the image pick-up device 141 are sent to the image processor unit 500 of the processor 200 via a cable 142.

The image processor unit 500 comprises an A/D conversion circuit 510, a temporary memory 520, a controller 530, a video memory 540 and a signal processing circuit 550. The A/D conversion circuit 510 executes A/D conversion to the image signals transmitted from the image pick-up device 141 of the electronic endoscope 100 via the cable 142 to output digital image data. The digital image data outputted from the A/D conversion circuit 510 is transmitted to and stored in the temporary memory 520. The digital image data includes R digital image data which is captured by the light-receiving element to which the R filter is provided, G digital image data which is captured by the light-receiving element to which the G filter is provided, and B digital image data which is captured by the light-receiving element to which the B filter is provided.

The controller 530 processes a piece of or a plurality of pieces of image data stored in the temporary memory 520 to generate one piece of display image data, and transmits the display image data to the video memory 540. For example, the controller 530 generates display image data such as display image data generated from a piece of digital image data, display image data in which a plurality of pieces of image data are arranged, or display image data in which healthy regions and lesion regions are identified or a graph of a reflection spectrum of the biological tissue T corresponding to a specific pixel (x, y) is displayed by generating a reflection spectrum of the biological tissue T for each pixel (x, y) on the basis of a plurality of pieces of digital image data, and stores them in the video memory 540. The signal processing circuit 550 generates video signals having a predetermined format (e.g., a format which conforms to NTSC or DVI standard) on the basis of the display image data stored in the video memory 540, and outputs the video signals. The video signals outputted from the signal processing circuit 550 are inputted to the monitor 300. As a result, endoscopic images taken by the electronic endoscope 100 and the like are displayed on the monitor 300.

As described above, the processor 200 has both a function as a video processor for processing the image signals outputted from the image pick-up device 141 of the electronic endoscope 100, and a function as a light source device for supplying illumination light IL to the light guide 131 of the electronic endoscope 100 to illuminate the biological tissue T being an object.

Other than the above-mentioned light source 430, the light source unit 400 comprises a collimator lens 440, a rotating filter 410, a filter control unit 420 and a condenser lens 450. The white light WL emitted from the light source 430 is converted by the collimator lens 440 into a collimated beam, transmits through the rotating filter 410, and then is incident on the end portion 131b of the light guide 131 by the condenser lens 450. The rotating filter 410 is movable between an applied position on an optical path of the white light WL and a retracted position shifted from the optical path by a moving mechanism (not shown) such as a linear guide way.

The rotating filter 410 is a circular plate type optical unit comprising a plurality of optical filters, and is configured such that a transmission wavelength range thereof changes in accordance with the rotation angle thereof. The rotation angle of the rotating filter 410 is controlled by the filter control unit 420 connected to the controller 530. The spectrum of the illumination light supplied to the light guide 131 through the rotating filter 410 can be switched by the controller 530 controlling the rotation angle of the rotating filter 410 via the filter control unit 420.

Figure 4:
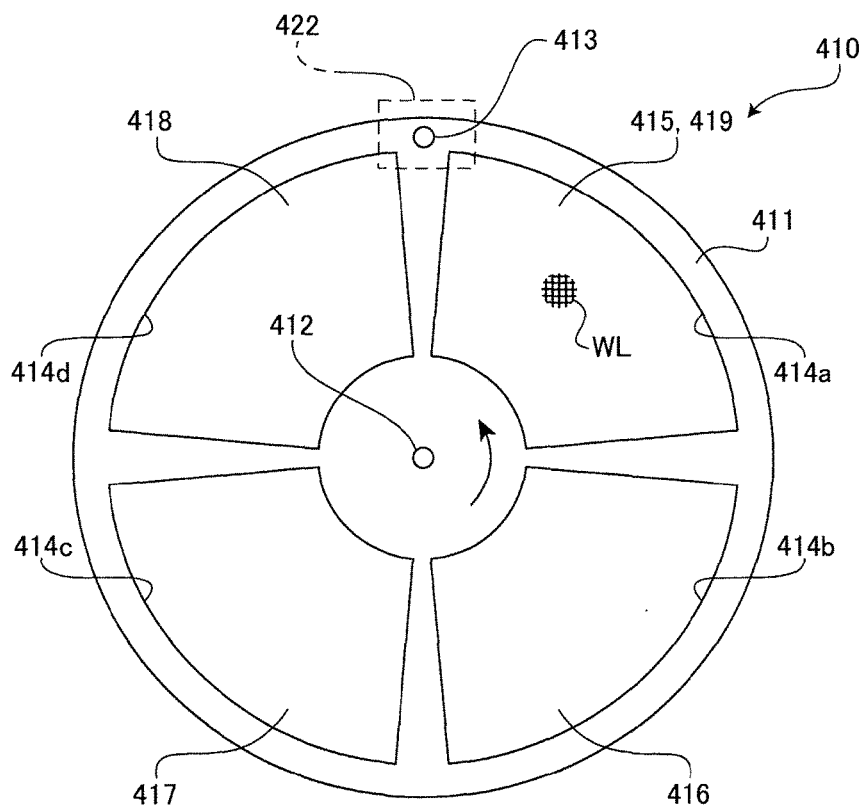
FIG. 4 illustrates an outer appearance of a rotating filter provided in the endoscope device.

FIG. 4 is an external view (front view) of the rotating filter 410. The rotating filter 410 comprises a substantially circular plate shaped frame 411, and four fan-shaped optical filters 415, 416, 417, and 418. Around the central axis of the frame 411, four fan-shaped windows 414a, 414b, 414c, and 414d are formed at regular intervals, and the optical filters 415, 416, 417, and 418 are fit into each of the windows 414a, 414b, 414c, and 414d, respectively. It is noted that, although the optical filters of the present embodiment are all dielectric multilayer film filters, other types of optical filters (e.g., absorbing type optical filters or etalon filters in which dielectric multilayers are used as reflecting layers) may also be used.

Also, a boss hole 412 is formed on the central axis of the frame 411. An output axis of a servo motor (not shown) included in the filter control unit 420 is inserted and fixed to the boss hole 412, and the rotating filter 410 rotates along with the output axis of the servo motor.

FIG. 4 shows a state in which the white light WL is incident on the optical filter 415. However, as the rotating filter 410 rotates in a direction indicated by an arrow, the optical filter on which the white light WL is incident changes to 415, 416, 417, 418 in this order, and thus the spectrum of the illumination light IL that transmits the rotating filter 410 can be switched.

The optical filters 415 and 416 are optical band-pass filters that selectively transmit light of 550 nm band. As shown in FIG. 1, the optical filter 415 is configured to transmit light which is inside the wavelength range between isosbestic points E1 and E4 (i.e., a wavelength range R0 which is also referred to as a "first illumination wavelength range") with low loss, and to cut off light which is outside the wavelength range. Also, the optical filter 416 is configured to transmit light which is inside the wavelength range between isosbestic points E2 and E3 (i.e., wavelength range R2 which is also referred to as a "second illumination wavelength range") with low loss, and to cut off light which is outside the wavelength range.

As shown in FIG. 1, in the wavelength range R0, the peak wavelength of the absorption peak P1 which derives from oxyhemoglobin is included. In the wavelength range R2, the peak wavelength of the absorption peak P2 which derives from deoxyhemoglobin is included. In the wavelength range R3, the peak wavelength of the absorption peak P3 which derives from oxyhemoglobin is included. Further, in the wavelength range R0, the peak wavelengths of the absorption peaks P1, P2 and P3 are included.

Figure 3:
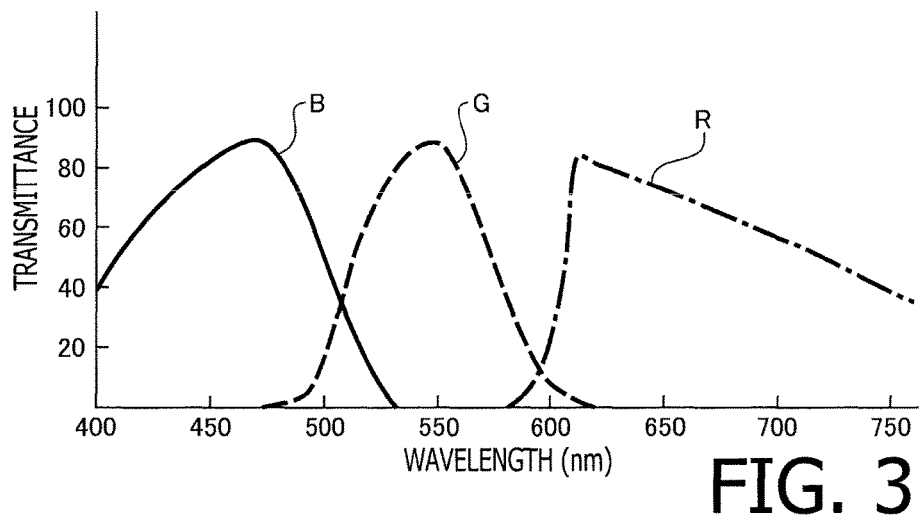
FIG. 3 is a graph illustrating a spectral property of a color filter embedded in an image pick-up device provided in the endoscope device.

The transmission wavelength ranges of the optical filters 415 and 416 (FIG. 1) are included in a transmission wavelength range of the G filter of the color filter 141a (FIG. 3). Therefore, an image which is formed by light that transmitted through the optical filter 415 or 416 is captured by the light-receiving element to which the G filter is provided, and is acquired as the G digital image data.

The optical filter 417 is designed to selectively transmit only light of 650 nm band (630-650 nm) being a wavelength range in which an absorbance of hemoglobin in the biological tissue T is low. The transmission wavelength range of the optical filter 417 is included in a transmission wavelength range of the R filter of the color filter 141a (FIG. 3). Therefore, an image which is formed by light that transmitted through the optical filter 417 is captured by the light-receiving element to which the R filter is provided, and is acquired as the R digital image data. The image data acquired by using the illumination light of 650 nm band is used in a standardization process which will be explained later.

Also, the optical filter 418 is an ultraviolet cut filter, and the illumination light IL (i.e., white light) that transmitted through the optical filter 418 is used for capturing normal observation images. It is noted that the rotating filter 410 may be configured without the optical filter 418 to leave the window 414d of the frame 411 open.

To the window 414a, a dimmer filter 419 (ND filter) is provided over the optical filter 415. The dimmer filter 419 does not have wavelength dependency throughout the visible light range and thus only decreases a light amount of the illumination light IL without changing the spectrum thereof. The light amount of the illumination light IL that transmitted through the optical filter 415 and the dimmer filter 419 are adjusted to a light amount substantially equivalent to a light amount of the illumination light IL that transmitted through the optical filter 416 by using the dimmer filter 419. Thus, images can be captured with a proper exposure with the same exposure time in both a case where the illumination light IL that passed through the optical filter 415 is used and a case where the illumination light IL that passed through the optical filter 416 is used.

In the present embodiment, a metal mesh having a fine mesh size is used as the dimmer filter 419. Apart from the metal mesh, other types of dimmer filter such as a half mirror type may be used. Further, transmittances of the optical filters 415 and 416 themselves may be adjusted instead of using the dimmer filter. Further, dimmer filters may also be provided to the windows 414c and 414d. Further, central angles of the windows 414a, 414b, 414c, and 414d (i.e., aperture areas) may be changed to adjust transmitting light amounts. Further, the exposure time may be changed for each optical filter instead of using the dimmer filter.

At the periphery of the frame 411, a through hole 413 is formed. The through hole 413 is formed at a position that is same as a position of boundary between the windows 414a and 414d in the rotating direction of the frame 411. Around the frame 411, a photo interrupter 422 for detecting the through hole 413 is arranged such that the photo interrupter 422 surrounds a portion of the periphery of the frame 411. The photo interrupter 422 is connected to the filter control unit 420.

The endoscope device 1 of the present embodiment has a normal observation mode, a spectral analysis (oxygen saturation distribution image displaying) mode, a baseline measuring mode and a calibration mode. The normal observation mode is an operation mode in which a color image is captured using white light that transmitted through the optical filter 418. The spectral analysis mode is a mode in which a spectral analysis is carried out on the basis of the digital image data captured using illumination light that transmitted through the optical filters 415, 416 and 417, and a distribution image of biomolecules in a biological tissue (e.g., oxygen saturation distribution image) is displayed. The baseline measuring mode is a mode in which an image of a color reference board such as a colorless diffusion board (e.g., frosted glass) or a reference reflection board is captured as an object using illumination light that passed through the optical filters 415, 416 and 417, before (or after) executing the actual endoscopic observation, to acquire data to be used in a standardization process which will be described later. The calibration mode is a process in which a spectral analysis is carried out for a sample of which properties such as the oxygen saturation is known, and a parameter (correction coefficient k which will be described later) is adjusted such that there is no difference between the analysis result and the theoretical value.

In the normal observation mode, the controller 530 controls the moving mechanism to move the rotating filter 410 from the applied position to the retracted position. In the operation modes other than the normal observation mode, the rotating filter 410 located at the applied position. In the case where the rotating filter 410 is not proved with the moving mechanism, the controller 530 controls the filter control unit 420 to immobilize the rotating filter 410 at a position where the white light WL is incident on the optical filter 418. Then, the digital image data captured by the image pick-up device 141 is converted to video signals after performing image processes as necessary, and is displayed on the monitor 300.

In the spectral analysis mode, the controller 530 controls the filter control unit 420 to drive the rotating filter 410 to rotate at constant rotation speed while sequentially capturing images of the biological tissue T using illumination light that transmitted through the optical filters 415, 416, 417 and 418. Then, an image indicating distribution of biomolecules in the biological tissue is generated on the basis of digital image data acquired using each of the optical filters 415, 416 and 417. Then, a display image in which the distribution image and a normal observation image acquired by using the optical filter 418 are arranged is generated and converted to video signals, and is displayed on the monitor 300.

In the spectral analysis mode, the filter control unit 420 detects a rotational phase of the rotating filter 410 on the basis of timing the photo interrupter 422 detects the through hole 413, compares the rotational phase to a phase of a timing signal supplied by the controller 530, and adjusts the rotational phase of the rotating filter 410. The timing signal from the controller 530 is synchronized with a driving signal for the image pick-up device 141. Therefore, the rotating filter 410 is driven to rotate at a substantially constant rotation speed in synchronization with the driving of the image pick-up device. Specifically, the rotation of the rotating filter 410 is controlled such that the optical filter 415, 416, 417 or 418 (window 414a, b, c or d) on which the white light WL is to be incident switches each time one image (three frames: R, G and B) is captured by the image pick-up device 141.

In the baseline measuring mode, the controller 530 controls the filter control unit 420 to rotate the rotating filter 410 while sequentially capturing images of the color reference board using the illumination light IL that transmitted through the optical filters 415, 416 and 417. Each piece of the G digital image data captured using the illumination light IL that transmitted through the optical filters 415 and 416 is stored in an internal memory 531 of the controller 530 as baseline image data $BL_{415}$ (x, y) and $BL_{416}$ (x, y), respectively. Further, the R digital image data captured using the illumination light IL that transmitted through the optical filter 417 is stored in the internal memory 531 of the controller 530 as baseline image data $BL_{417}$ (x, y).

Figure 5:
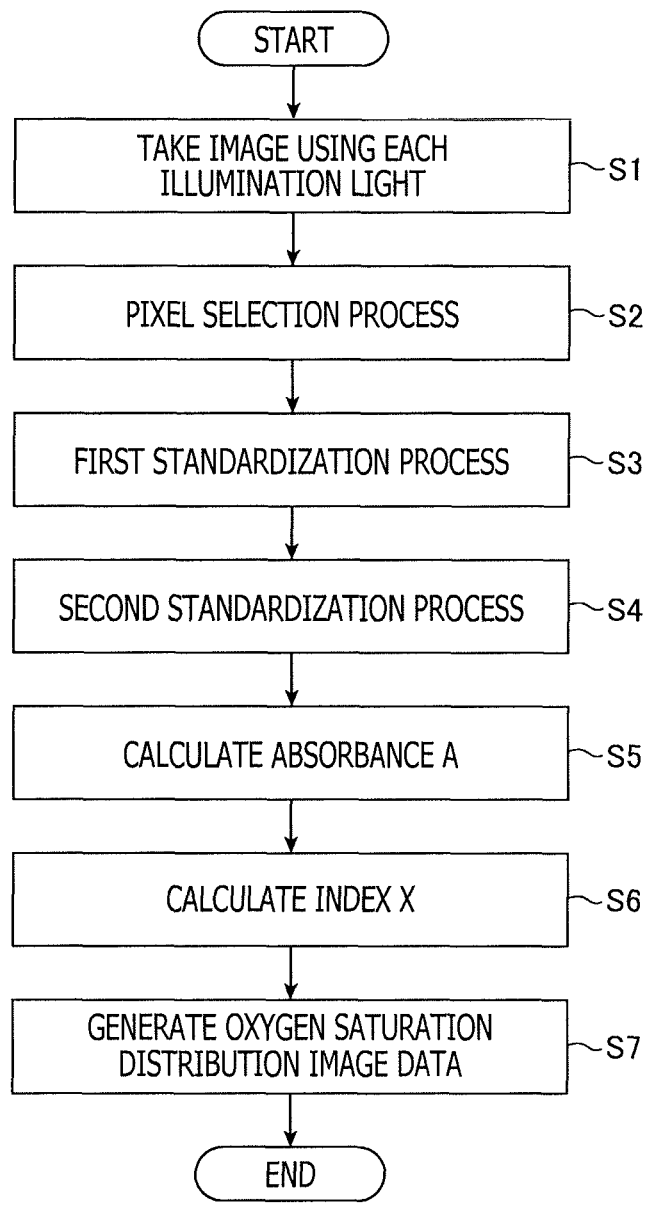
FIG. 5 is a flowchart illustrating an image generation process according to the embodiment of the invention.

Next, an image generation process executed by the image processor unit 500 in the spectral analysis mode will be described. Since, in this embodiment, the image processor unit 500 calculates the index X, the image processor unit 500 may be referred to as an index calculation unit. FIG. 5 is a flow chart explaining the image generation process.

When the spectral analysis mode is selected by a user's operation, as described above, the filter control unit 420 drives the rotating filter 410 to rotate at constant rotation speed. Then, from the light source unit 400, the illumination light IL that transmitted through the optical filters 415, 416, 417 and 418 are sequentially supplied, and an image is sequentially captured using each of the illumination light IL (S1). Specifically, G digital image data $G_{415}$ (x, y) captured using the illumination light IL that transmitted through the optical filter 415, G digital image data $G_{416}$ (x, y) captured using the illumination light IL that transmitted through the optical filter 416, R digital image data $R_{417}$ (x, y) captured using the illumination light IL that transmitted through the optical filter 417, and R digital image data $R_{418}$ (x, y), G digital image data $G_{418}$ (x, y) and B digital image data $B_{418}$ (x, y) captured using the illumination light IL that transmitted through the optical filter (ultraviolet cut filter) 418 are stored in an internal memory 532 of the controller 530.

Then, the image processor unit 500 executes a pixel selection process S2 for selecting pixels to be targets of the following analyzing processes (processes S3-S7) by using the R digital image data $R_{418}$ (x, y), G digital image data $G_{418}$ (x, y) and B digital image data $B_{418}$ (x, y) acquired in the process S1. Even if the oxygen saturations or blood flow rates are calculated from color information of pixels corresponding to portions which do not contain blood or portions which colors of tissues are dominantly influenced by substances other than hemoglobin, meaningful values cannot be obtained and thus the values become mere noises. Calculating and providing such noises not only disturbs diagnosis by the doctor but also causes a bad effect by applying useless load to the image processor unit 500 to deteriorate processing speed. Therefore, the image generating process of the present embodiment is configured to select pixels that are appropriate to the analyzing process (i.e., pixels to which the spectral property of hemoglobin is recorded) and to execute the analyzing process to the selected pixels.

In the pixel selection process S2, only pixels which satisfy all the conditions expressed in expression (19), expression (20) and expression (21) are selected as the targets of the analyzing process.

$$B_{418}(x,y)/G_{418}(x,y) > a_1 \qquad (19)$$

$$R_{418}(x,y)/G_{418}(x,y) > a_2 \qquad (20)$$

$$R_{418}(x,y)/B_{418}(x,y) > a_3 \qquad (21)$$

where $a_1$, $a_2$ and $a_3$ are positive constants.

The above three conditional expressions are set on the basis of a value size relation, G component<B component<R component, in a transmission spectrum of blood. It is noted that the pixel selection process S2 may be executed using one or two of the above three conditional expressions (e.g., using Expression 12 and Expression 13 by focusing on a red color that is specific to blood).

Then, the image processor unit 500 executes the standardization process. The standardization process of the present embodiment includes a first standardization process S3 for correcting properties of the endoscope device 1 itself (e.g., transmittances of the optical filters and light receiving sensitivities of the image pick-up devices) and a second standardization process S4 for correcting reflectivity variations due to differences in surface states of the biological tissue T being an object and due to angles of incidence of the illumination light to the biological tissue T.

In the standardization process, the image processor unit 500 calculates a standardized reflectivity $SR_{415}$ (x, y) using the following expression (22) by using the G digital image data $G_{415}$ (x, y) taken using the illumination light IL that transmitted through the optical filter 415, the R digital image data $R_{417}$ (x, y) taken using the illumination light IL that transmitted through the optical filter 417, and the baseline image data $BL_{415}$ (x, y) and $BL_{417}$ (x, y). It is noted that a component that is dependent on the properties of the endoscope device 1 (instrumental function) is removed by dividing each of the digital image data $G_{415}$ (x, y) and $R_{417}$ (x, y) by the respective baseline image data $BL_{415}$ (x, y) and $BL_{417}$ (first standardization process S3). Also, the reflectivity variations due to differences in surface states of the biological tissue T and angles of incidence of the illumination light to the biological tissue T is corrected by dividing the G digital image data $G_{415}$ (x, y) by the R digital image data $R_{417}$ (x, y) (second standardization process S4).

$$SR_{415}(x, y) = \frac{G_{415}(x, y)/BL_{415}(x, y)}{R_{417}(x, y)/BL_{417}(x, y)} \quad (22)$$

Similarly, a standardized reflectivity $SR_{416}$ (x, y) is calculated using the following expression (23).

$$SR_{416}(x, y) = \frac{G_{416}(x, y)/BL_{416}(x, y)}{R_{417}(x, y)/BL_{417}(x, y)} \quad (23)$$

Absorbances $A_{415}$ (x, y) and $A_{416}$ (x, y) of the biological tissue T with respect to the illumination light IL that transmitted through the optical filters 415 and 416 are calculated using the following expressions (24) and (25) (S5).

$$A_{415}(x,y) = -\log[SR_{415}(x,y)] \quad (24)$$

$$A_{416}(x,y) = -\log[SR_{416}(x,y)] \quad (25)$$

It is noted that the absorbances $A_{415}$ (x, y) and $A_{416}$ (x, y) can be approximately calculated using the following expressions (26) and (27).

$$A_{415}(x,y) = -SR_{415}(x,y) \quad (26)$$

$$A_{416}(x,y) = -SR_{416}(x,y) \quad (27)$$

Furthermore, the spectral analysis can be executed simply by eliminating the above mentioned standardization processes (S3, S4). In this case, the absorbances $A_{415}$ (x, y) and $A_{416}$ (x, y) are calculated using the following expressions (28) and (29).

$$A_{415}(x,y) = -\log G_{415}(x,y) \quad (28)$$

$$A_{416}(x,y) = -\log G_{416}(x,y) \quad (29)$$

Also, in this case, the absorbances $A_{415}$ (x, y) and $A_{416}$ (x, y) can be approximately calculated using the following expressions (30) and (31), respectively.

$$A_{415}(x,y) = -G_{415}(x,y) \quad (30)$$

$$A_{416}(x,y) = -G_{416}(x,y) \quad (31)$$

Furthermore, as is obvious from the relationships between the absorption wavelength ranges R1, R2 and R3 of hemoglobin and the transmission wavelength ranges of the optical filters 415 and 416 shown in FIG. 1, absorbances $A_{R1}$ (x, y), $A_{R2}$ (x, y) and $A_{R3}$ (x, y) of the biological tissue T with respect to the wavelength ranges R1, R2 and R3 and the absorbances $A_{415}$ (x, y) and $A_{416}$ (x, y) of the biological tissue T with respect to the illumination light IL that transmitted through the optical filters 415 and 416 have relationships expressed in the following expressions (32) and (33).

$$A_{R1}(x,y) + A_{R3}(x,y) = A_{415}(x,y) - kA_{416}(x,y) \quad (32)$$

$$A_{R2}(x,y) = kA_{416}(x,y) \quad (33)$$

Therefore, the index X (expression (18)) is expressed by the following expression (34).

$$X(x, y) = [A_{R1}(x, y) + A_{R3}(x, y)] - A_{R2}(x, y) \quad (34)$$

$$= [A_{415}(x, y) - kA_{416}(x, y)] - kA_{416}(x, y)$$

$$= A_{415}(x, y) - 2kA_{416}(x, y)$$

Here, k is a constant (correction coefficient). Since the width of the transmission wavelength ranges of the optical filters 415 and 416 differ significantly, the light amounts that transmit through the two filters also differ significantly. Therefore, as mentioned above, the dimmer filter 419 is provided over the optical filter 415, which has a large transmitting light amount, to control the light amount so that a proper exposure can be obtained with the same exposure time even if the optical filter is switched. As a result, a quantitative relationship between the absorbance $A_{415}$ (x, y) acquired using the optical filter 415 and the absorbance $A_{416}$ (x, y) acquired using the optical filter 416 is broken. Also, the transmittances of the optical filters 415 and 416 within the transmission wavelength ranges are not 100% and the optical filters 415 and 416 have transmission losses that vary depending thereon. Furthermore, there are errors in the transmission wavelength ranges of the optical filters 415 and 416. Therefore, even if the dimmer filter 419 is not used, the quantitative relationship between the absorbance $A_{415}$ (x, y) and the absorbance $A_{416}$ (x, y) includes a constant error. The correction coefficient k is a constant for correcting the error of the quantitative relationship between the absorbance $A_{415}$ (x, y) and the absorbance $A_{416}$ (x, y). A method for acquiring the correction coefficient k will be described later. It is noted that, in case this correction is not executed, the correction coefficient is set at 1.

Further, the following expression (35) can be obtained by arranging the expression (34) using expressions (24) and (25).

$$X(x, y) = -\log[SR_{415}(x, y)] + 2k\log[SR_{416}(x, y)] \quad (35)$$

$$= -\log\left[\frac{G_{415}(x, y)/BL_{415}(x, y)}{R_{417}(x, y)/BL_{417}(x, y)}\right] +$$

$$2k\log\left[\frac{G_{416}(x, y)/BL_{416}(x, y)}{R_{417}(x, y)/BL_{417}(x, y)}\right]$$

$$= -\{[\log G_{415}(x, y) - \log BL_{415}(x, y)] - +$$

$$[\log R_{417}(x, y) - \log BL_{417}(x, y)]\}$$

$$2k\{[\log G_{416}(x, y) - \log BL_{416}(x, y)] -$$

$$[\log R_{417}(x, y) - \log BL_{417}(x, y)]\}$$

$$= -[\log G_{415}(x, y) - \log BL_{415}(x, y)] +$$

$$2k[\log G_{416}(x, y) - \log BL_{416}(x, y)] +$$

$$(1 - 2k)[\log R_{417}(x, y) - \log BL_{417}(x, y)]$$

Therefore, the value of index X can be calculated from the G digital image data $G_{415}$ (x, y) and $G_{416}$ (x, y), R digital image data $R_{8417}$ (x, y), and the baseline image data $BL_{415}$ (x, y), $BL_{416}$ (x, y) and $BL_{417}$ (x, y) by using the expression (35) (S6).

Further, the index X can also be approximately calculated using the following expression (36).

$$X(x,y) = -\log [SR_{415}(x,y)] + 2k \log [SR_{416}(x,y)] \approx -SR_{415}(x,y) + 2kSR_{416}(x,y) \quad (36)$$

A value list indicating the quantitative relationship between the oxygen saturation and the index X experimentally acquired in advance is stored in a non-volatile memory 532 provided to the controller 530. The controller 530 refers to this value list to acquire an oxygen saturation $SatO_2$ (x, y) which corresponds to a value of the index X calculated using the expression (35) or (36). Then, the controller 530 generates image data (oxygen saturation distribution image data) of which pixel value of each pixel (x, y) is a value obtained by multiplying the acquired oxygen saturation $SatO_2$ (x, y) by a predetermined value (S7).

Also, the controller 530 generates normal observation image data from the R digital image data $R_{418}$ (x, y), G digital image data $G_{418}$ (x, y) and B digital image data $B_{418}$ (x, y) acquired using the illumination light IL that transmitted through the optical filter (ultraviolet cut filter) 418.

Figure 7A:
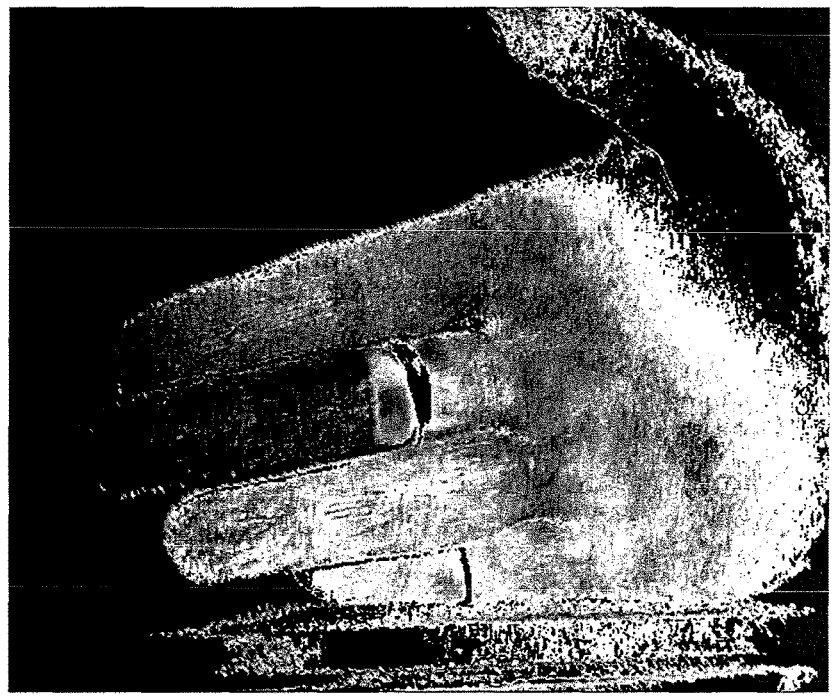
Figure 7B:
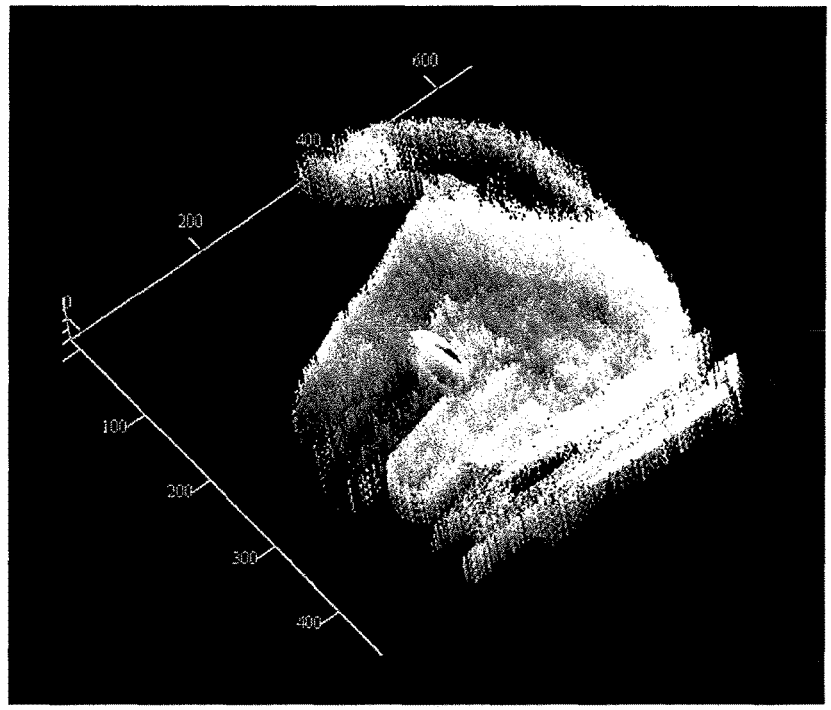

FIGS. 7A and 7B show display examples of image data generated by the controller 530. FIG. 7A is a display example of the oxygen saturation distribution image data (two-dimensional representation) generated in the above described process S7. FIG. 7B is a display example of the oxygen saturation distribution image data (three-dimensional representation) generated in a three-dimensional graph style having the vertical axis representing the oxygen saturation. Each of FIGS. 7A and 7B shows the observation image of the right hand in a state where the middle finger is pressed by a rubber band in the vicinity of the proximal interphalangeal joint. It is understood that the oxygen saturation becomes lower on the distal side of the right middle finger with respect to the pressed portion because the blood flow is obstructed by the pressure.

Further, the controller 530 generates screen image data for arranging and displaying the normal observation image and the oxygen saturation distribution image on a single screen from the generated oxygen saturation distribution image data and normal observation image data, and stores the screen data in the video memory 540. It is noted that the controller 530 can generate a variety of screen images such as a screen image that only displays the oxygen saturation distribution image, a screen image that only displays the normal observation image, or a screen image on which associated information such as patient's ID information or observation condition is superimposed on the oxygen saturation distribution image and/or the normal observation image in accordance with the user's operations.

Next, a method for determining the correction coefficient k in the calibration mode will be described. In the present embodiment, a theoretically calculated index X and a measured index X are compared, and the correction coefficient k is determined such that the measured index X becomes closest to the theoretically calculated index X.

Figure 6A:
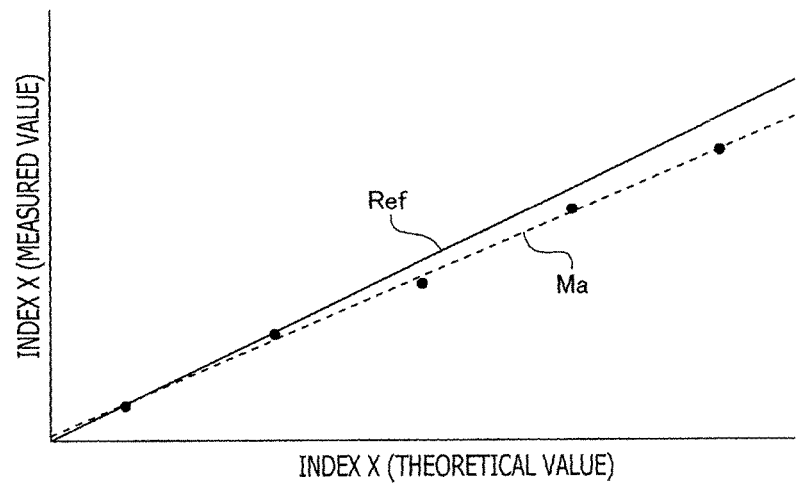
FIGS. 6A and 6B show exemplary calibration curves used for determining a correction coefficient k.
Figure 6B:
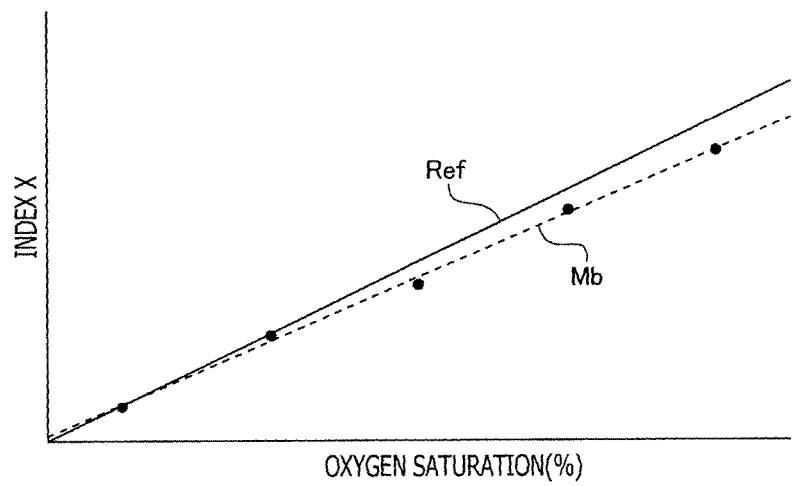

FIGS. 6A and 6B show exemplary calibration curves used to determine the correction coefficient k in the embodiment of the present invention. FIG. 6A is an example of a common calibration curve of which the horizontal axis is the theoretical index X and the vertical axis is the measured index X acquired by the above explained analyzing process. The filled circles are plots of the measured values, and the broken line Ma is a straight line fitted to the measured value by a least-square method. Further, the solid line shows a reference line Ref representing plots in case measured values equivalent to the theoretical values are obtained.

The measured index X is acquired by the analyzing process using a sample of a biological tissue of which the oxygen saturation is known (e.g., blood). Further, the theoretical index X defined by the expression (34) is calculated using transmission spectra of the optical filters 415 and 416 to be actually used and a reflection spectrum (or absorption spectrum) of blood. Specifically, the theoretical index X is calculated using the expression (34) by using a value obtained by multiplying the transmission spectrum of the optical filter 415 (optical filter 416) by the reflection spectrum of blood and integrating the product as the absorbance $A_{415}$ (absorbance $A_{416}$).

A discrepancy between the Reference line Ref and the measured value Ma is expressed as a gradient of the calibration curve. A phenomenon of which sufficient sensitivity cannot be obtained, that is, a phenomenon of which the gradient is small, is due to an inappropriate quantitative relationship between the absorbance $A_{415}$ (x, y) and the absorbance $A_{416}$ (x, y) in the expression (34), caused by the use of the dimmer filter 419. By selecting an appropriate value as the correction coefficient k, an error caused by the dimmer filter 419 can be corrected, and thus a state in which an error between the measured index X and the theoretical index X is minimized and the measured index X has the highest correlational relationship with the theoretical index X can be achieved.

FIG. 6B is a variation of the calibration curve. In the calibration curve shown in FIG. 6B, the horizontal axis is the oxygen saturation of a sample, and the vertical axis is the index X. The filled circles are plots of the measured values, and the broken line Mb is a straight line fitted to the measured value by a least-square method. Further, the solid line Rref shows the theoretically calculated values. It is noted that the oxygen saturations of the sample are correctly measured values acquired from an ideal spectrometry. Being a curve obtained by changing the horizontal scale of the calibration curve shown in FIG. 6A, this calibration curve is substantially equivalent to the curve of FIG. 6A, but there is an advantage that a correct relationship with the oxygen saturation can be easily read.

It is noted that, although the above-explained method for determining the correction coefficient k using the calibration curve is a method in which analysis results of a plurality of samples having different oxygen saturations are used, the correction coefficient k can also be determined using an analysis result from only one sample.

Also, focusing on the absorption wavelength ranges R1, R2 and R3 of hemoglobin (i.e., the transmission wavelength of the optical filter 415), the absorbances $A_{R1}$ (x, y), $A_{R2}$ (x, y) and $A_{R3}$ (x, y) change in accordance with the change in the oxygen saturation, but a sum Y of these absorbances (shown in the expression (37)) is substantially constant. Furthermore, since the sum Y of the absorbances is in proportion to a total amount of hemoglobin (a sum of oxyhemoglobin $HbO_2$ and deoxyhemoglobin Hb) in a biological tissue, it is reasonable to use the sum Y as an index for the total amount of hemoglobin.

$$Y(x,y) = A_{R1}(x,y) + A_{R2}(x,y) + A_{R3}(x,y) = A_{415} \quad (37)$$

It is known that, in a tissue of a malignant tumor, the total amount of hemoglobin is greater than that of a healthy tissue due to angiogenesis and the oxygen saturation is lower than that of a healthy tissue due to notable oxygen metabolism. Therefore, the controller 530 can extract pixels of which the index Y, calculated using the expression (37) and indicating the total amount of hemoglobin, is greater than a predetermined reference value (first reference value) and the index X, calculated using the expression (34) and indicating the oxygen saturation, is smaller than a predetermined reference value (second reference value); generate, for example, lesion region highlighting image data in which highlighting process is executed to pixels corresponding to the extracted pixels in the normal observation image data; and display the lesion region highlighting image along with the normal observation image and/or the oxygen saturation distribution image (or alone) on the monitor 300.

Exemplary highlighting process includes a process for increasing pixel values of corresponding pixels, a process for changing color phases (for example, a process for increasing the R component to change to a reddish color or a process for rotating the color phase for a predetermined angle), and a process for making the corresponding pixels blink (or periodically changing the color phase).

Further, for example, the controller 530 may be configured to calculate an index Z (x, y) indicating a probability of being a malignant tumor on the basis of a deviation from an average of the index X (x, y) and a deviation from an average of the index y (x, y), and to generate image data with the index Z as pixel values (malign probability image data) instead of the lesion region highlighting image data.

Variation 1

Hereafter, a variation 1 of the above described embodiment of the invention is described. In the above described embodiment, as expressed in the expression 18, the index X is calculated by adding together the absorbances $A_{R1}$, $A_{R2}$ and $A_{R3}$ at the wavelength ranges R1, R2 and R3 while not weighting the absorbances $A_{R1}$, $A_{R2}$ and $A_{R3}$ although signs thereof are adjusted such that increase or decrease in the respective wavelength ranges match with each other. By contrast, according to the variation 1, by weighting the absorbances $A_{R1}$, $A_{R2}$ and $A_{R3}$ at the respective wavelength ranges when the index X is calculated, sensitivity of the index X with respect to change of the oxygen saturation is enhanced.

As shown in FIG. 1, in the wavelength range R2, the fluctuation range of absorbance with respect to the oxygen saturation is larger than that in the fluctuation ranges R1 and R2. Therefore, by increasing the weight applied to the absorbance $A_{R2}$ at the wavelength range R2, the sensitivity of the index X with respect to the oxygen saturation can be enhanced.

Specifically, the index X is calculated according to the following expression (38) while applying the two-fold weight to the absorbance $A_{R2}$.

$$X(x, y) = [A_{R1}(x, y) + A_{R3}(x, y)] - 2 \times A_{R2}(x, y) \quad (38)$$

$$= [A_{415}(x, y) - kA_{416}(x, y)] - 2kA_{416}(x, y)$$

$$= A_{415}(x, y) - 3kA_{416}(x, y)$$

$$= -\log[SR_{415}(x, y)] + 3k\log[SR_{416}(x, y)]$$

$$= -\log\left[\frac{G_{415}(x, y)/BL_{415}(x, y)}{R_{417}(x, y)/BL_{417}(x, y)}\right] +$$

$$3k\log\left[\frac{G_{416}(x, y)/BL_{416}(x, y)}{R_{417}(x, y)/BL_{417}(x, y)}\right]$$

$$= -\{[\log G_{415}(x, y) - \log BL_{415}(x, y)] - [\log R_{417}(x, y) - \log BL_{417}(x, y)]\}$$

$$3k\{[\log G_{416}(x, y) - \log BL_{416}(x, y)] - [\log R_{417}(x, y) - \log BL_{417}(x, y)]\}$$

$$= -[\log G_{415}(x, y) - \log BL_{415}(x, y)] +$$

$$3k[\log G_{416}(x, y) - \log BL_{416}(x, y)] +$$

$$(1 - 3k)[\log R_{417}(x, y) - \log BL_{417}(x, y)]$$

The index X may be calculated approximately by the following expression (39).

$$X(x,y) = -\log[SR_{415}(x,y)] + 3k \log[SR_{416}(x,y)] \cong -SR_{415}(x,y) + 3kSR_{416}(x,y) \quad (39)$$

In the above described variation 1, the 2-fold weighting is applied to the absorbance $A_{R2}$ with respect to the absorbances $A_{R1}$ and $A_{R3}$; however, the weighting value may be changed appropriately to a different value (e.g., 1.5-fold or 2.4-fold) such that suitable sensitivity or a noise amount is attained. By generalizing the expression 38 such that the weights of the absorbances $A_{R1}$ and $A_{R3}$ are w1 and the weight of the absorbance $A_{R2}$ is w2, the index X can be expressed by the following expression (40).

$$X(x, y) = w1 \times [A_{R1}(x, y) + A_{R3}(x, y)] - w2 \times A_{R2}(x, y) \quad (40)$$

$$= w1 \cdot [A_{415}(x, y) - kA_{416}(x, y)] - w2 \cdot k \cdot A_{416}(x, y)$$

$$= w1 \cdot A_{415}(x, y) - k \cdot (w1 + w2) \cdot A_{416}(x, y)$$

$$= -w1 \cdot \log[SR_{415}(x, y)] + k \cdot (w1 + w2) \cdot$$

$$\log[SR_{416}(x, y)]$$

The index X may be obtained approximately by the following expression (41).

$$X(x,y) \cong w1 \cdot SR_{415}(x,y) + k \cdot (w1+w2) \cdot SR_{416}(x,y) \quad (41)$$

Variation 2

Hereafter, a variation 2 of the above described embodiment is described. In the above described embodiment, the index X is calculated by the difference between the sum of the absorbances $A_{R1}$ and $A_{R3}$ at the wavelength ranges R1 and R3 where the absorbance increases with the oxygen saturation, and the absorbance $A_{R2}$ at the wavelength range R2 where the absorbance decreases with the oxygen saturation. By contrast, according to the variation 2, the index X is calculated by the ratio between the absorbance $A_{R2}$ and the sum of the absorbances $A_{R1}$ and $A_{R3}$. Specifically, the index X is calculated by the following expression (42).

$$X(x, y) = \frac{A_{R1}(x, y) + A_{R3}(x, y)}{A_{R2}(x, y)} \quad (42)$$

$$= \frac{A_{415}(x, y) - kA_{416}(x, y)}{kA_{416}(x, y)}$$

$$= \frac{A_{415}(x, y)}{kA_{416}(x, y)} - 1$$

$$= \frac{\log[SR_{415}(x, y)]}{k\log[SR_{416}(x, y)]} - 1$$

The index X may be obtained approximately by the following expression (43).

$$X(x, y) \cong \frac{SR_{415}(x, y)}{kSR_{416}(x, y)} - 1 \quad (43)$$

The index X may be calculated by applying the weight w1 to the sum of the absorbances $(A_{R1}+A_{R3})$ of the wavelength ranges R1 and R3 having the positive correlation with the oxygen saturation and applying the weight w2 to the absorbance $A_{R2}$ of the wavelength range R2 having negative correlation with the oxygen saturation by the following expression (44) or (45).

$$X(x, y) = \frac{w1 \cdot [A_{R1}(x, y) + A_{R3}(x, y)]}{w2 \cdot [A_{R2}(x, y)]} \quad (44)$$

$$= \frac{w1}{w2} \cdot \frac{A_{415}(x, y) - kA_{416}(x, y)}{k \cdot A_{416}(x, y)}$$

$$= \frac{w1}{w2} \cdot \left[\frac{A_{415}(x, y)}{kA_{416}(x, y)} - 1\right]$$

$$= \frac{w1}{w2} \cdot \left\{\frac{\log[SR_{415}(x, y)]}{k\log[SR_{416}(x, y)]} - 1\right\}$$

$$X(x, y) = \frac{[A_{R1}(x, y) + A_{R3}(x, y)]^{w1}}{[A_{R2}(x, y)]^{w2}} \quad (45)$$

$$= \frac{[A_{415}(x, y) - kA_{416}(x, y)]^{w1}}{[kA_{416}(x, y)]^{w2}}$$

$$= \frac{\{-\log[SR_{415}(x, y)] + k\log[SR_{416}(x, y)]\}^{w1}}{[kA_{416}(x, y)]^{w2}}$$

The absorbances $A_{R1}$ and $A_{R3}$ at the wavelength ranges R1 and R3 are in proportion to the concentration of oxyhemoglobin (i.e., the oxygen saturation $D_{SAT}$), and the absorbance $A_{R2}$ at the wavelength range R2 is in proportion to the concentration of deoxyhemoglobin (i.e., $1-D_{SAT}$). Therefore, from the first line of the expression 42, the following expression (46) is obtained.

$$X(x, y) = \frac{A_{R1}(x, y) + A_{R3}(x, y)}{A_{R2}(x, y)} \propto \frac{D_{Sat}(x, y)}{1 - D_{Sat}(x, y)} \quad (46)$$

Therefore, the index X calculated by the expression 46 becomes an index having suitable sensitivity to the oxygen saturation since the index X increases exponentially with increase of the oxygen saturation.

Variation 3

Hereafter, a variation 3 of the above described embodiment is described. In the above described embodiment, the dividing process is executed, in the second standardization process S4, using the R digital image data $R_{417}(x, y)$ captured using the illumination light IL in the band of 650 nm which has passed through the optical filter 417. However, the invention is not limited to such a configuration. For example, in the second standardization process S4, the dividing process may be executed by a sum of R, G and B digital image data captured using the illumination light IL which has passed through the optical filter 418 (or a dimmer filter or a transparent window without wavelength dependency).

In this case, the standardized reflectivity $SR_{415}(x, y)$ and $SR_{416}(x, y)$ are calculated by the following expressions (47) and (48), respectively.

$$SR_{415}(x, y) = \frac{G_{415}(x, y)/BL_{415}(x, y)}{\frac{R_{418}(x, y)}{BL_{R418}(x, y)} + \frac{G_{418}(x, y)}{BL_{G418}(x, y)} + \frac{B_{418}(x, y)}{BL_{B418}(x, y)}} \quad (47)$$

$$SR_{416}(x, y) = \frac{G_{416}(x, y)/BL_{416}(x, y)}{\frac{R_{418}(x, y)}{BL_{R418}(x, y)} + \frac{G_{418}(x, y)}{BL_{G418}(x, y)} + \frac{B_{418}(x, y)}{BL_{B418}(x, y)}} \quad (48)$$

Here, the baseline image data $BL_{R418}(x, y)$, $BL_{G418}(x, y)$ and $BL_{B418}(x, y)$ are R digital image data $R_{418}(x, y)$, G digital image data $G_{418}(x, y)$ and B digital image data $B_{418}(x, y)$ obtained by capturing the color reference board under illumination by the illumination light IL which has passed through the optical filter 418.

The foregoing is the explanation about specific configurations according to the embodiment of the invention; however, the present invention is not limited to the above described configuration and can be varied in various ways within the scope of the invention.

In the above described embodiment, the oxygen saturation is obtained from the value list based on the index X, and the pixel values of the oxygen saturation distribution image are calculated by further multiplying the oxygen saturation by a predetermined value. However, the present invention is not limited to such a configuration. Since the index X is monotonously increase with the oxygen saturation, the values of the index X (or values of the index X multiplied by a predetermined value) may be used as the pixel values of the oxygen saturation distribution image without change.

In the above described embodiment, it is explained that the image pick-up device 141 is an image pick-up device having an R, G and B primary color filter for picking up a color image; however, the present invention is not limited to such a configuration. For example, an image pick-up device having a complementary color filter of Y, Cy, Mg and G may be used as the image pick-up device 141.

In the above described embodiment, it is explained that the image pick-up device 141 is an image pick-up device having the on-chip color filter 141a for picking up a color image; however, the present invention is not limited to such a configuration. For example, the endoscope device may use an image pick-up device for picking up a monochrome image and may be provided with a so-called field sequential type color filter. Furthermore, the color filter 141a is not limited to the on-chip type, but may be disposed in an optical path from the light source 430 to the image pick-up device 141.

In the above described embodiment, the rotating filter 410 is used; however, the present invention is not limited to such a configuration. Another type of variable wavelength filter capable of switching transmission wavelength bands may be used.

In the above described embodiment, the rotating filter 410 is provided on the light source side, and filtering is performed for the illumination light IL; however, the present invention is not limited to such a configuration. The endoscope device may be configured such that the rotating filter 410 is disposed on the image pick-up device side (e.g., in a space between the objective optical system 121 and the image pick-up device 131), and filtering is performed for the returning light from the object.

In the above described embodiment, capturing is performed at predetermined time intervals while rotating the rotating filter 410 at a constant rotation number; however, the present invention is not limited to such a configuration. For example, the rotational position of the rotating filter 410 may be changed step by step at predetermined time intervals, and capturing may be performed when the rotating filter 410 is in a stationary state.

In the above described embodiment, the white light source, such as a Xenon lamp, is used as a light source for emitting wide bang light for illumination. However, a light source for emitting non-white wide band light having a sufficient amount of light over the entire transmission band of used optical filters may be employed.

For example, primary color light sources respectively emitting light having wavelengths of R, G and B may be provided, and light obtained by combining light of each of the primary color light sources may be used as the white light WL. In this case, a narrow band light source, such as a laser, may be used excepting the G primary color light source. As the G color light source, a light source emitting wide band light having a sufficient light amount at least in the entire of the first illumination light band (the wavelength range R0 in FIG. 1) is used.

In the above described embodiment, the transmission wavelength band R0 (the first illumination wavelength band) of the optical filter 415 includes the three peak wavelengths of the absorption peaks P1, P2 and P3. However, the first illumination wavelength band may include only two absorption peaks adjacent to each other (specifically, the absorption peaks P1 and P2 or the absorption peaks P2 and P3).

In the above described embodiment, the transmission type optical filter is used; however, a reflection type optical filter which reflects light in a transmission band may be used.

In the above described embodiment, the present invention is applied to an endoscope device which is an example of a device functioning as a digital camera. However, the present invention may be applied to a system having another type of digital camera (e.g., a single reflex digital camera or a digital video camera). For example, by applying the invention to a digital still camera, observation for a body surface tissue or observation for a brain tissue during craniotomy procedure can be performed.

This application claims priority of Japanese Patent Application No. P2014-236471, filed on Nov. 21, 2014. The entire subject matter of the application is incorporated herein by reference.

What is claimed is:

1. An analyzing device, comprising:
a light source device;
an image pick-up device that generates image data by capturing a biological tissue illuminated with light emitted by the light source device; and
a processor configured to calculate an index X representing a molar ratio between a first biological substance and a second biological substance contained in the biological tissue based on the image data,
wherein:
the light source device switches between light of a first illumination wavelength range which the first biological substance and the second biological substance absorb and light of a second illumination wavelength range lying within the first illumination wavelength range;
the processor is configured to calculate the index X based on first image data $G_1$ obtained by capturing the biological tissue under illumination of the light of the first illumination wavelength range and second image data $G_2$ obtained by capturing the biological tissue under illumination of the light of the second illumination wavelength range;
the first illumination wavelength range includes both of an absorption peak wavelength of the first biological substance and an absorption peak wavelength of the second biological substance; and
the second illumination wavelength range includes an absorption peak wavelength of one of the first biological substance and the second biological substance.

2. The analyzing device according to claim 1,
wherein the first illumination wavelength range includes:
a shorter wavelength side range which is situated to adjoin a shorter wavelength side edge of the second illumination wavelength range and includes an absorption peak of the other of the first biological substance and the second biological substance; and
a longer wavelength side range which is situated to adjoin a longer wavelength side edge of the second illumination wavelength range and includes an absorption peak of the other of the first biological substance and the second biological substance.

3. The analyzing device according to claim 1,
wherein the light source device comprises:
a light source that emits wide band light;
a first optical filter that selectively extracts the light of the first illumination wavelength range from the wide band light; and
a second optical filter that selectively extracts the light of the second illumination wavelength range from the wide band light.

4. The analyzing device according to claim 3,
wherein the processor operates to:
calculate an absorption $A_1$ of the biological tissue in the first illumination wavelength range based on the first image data $G_1$;
calculate an absorption $A_2$ of the biological tissue in the second illumination wavelength range based on the second image data $G_2$; and
calculate the index X based on the absorption $A_1$ and the absorption $A_2$.

5. The analyzing device according to claim 4,
wherein the processor calculates the absorption $A_1$ by one of following expressions (1) and (2):

$$A_1 = -\log G_1 \quad (1)$$

$$A_1 = -G_1 \quad (2),$$

wherein the processor calculates the absorption $A_2$ by one of following expressions (3) and (4):

$$A_2 = -\log G_2 \quad (3)$$

$$A_2 = -G_2 \quad (4).$$

6. The analyzing device according to claim 4,
wherein the processor calculates the index X by one of following expressions (5) and (6):

$$X = A_1 - 2kA_2 \quad (5)$$

$$X = A_1 - 3kA_2 \quad (6)$$

where k is a constant number.

7. The analyzing device according to claim 4,
wherein the processor calculates the index X by a following expression (7):

$$X = w1 \cdot A_1 - k \cdot (w1 + w2) \cdot A_2 \quad (7)$$

where k, w1 and w2 are constant numbers.

8. The analyzing device according to claim 4,
wherein the processor calculates the index X by a following expression (8):

$$X = \frac{w1}{w2} \cdot \left( \frac{A_1}{kA_2} - 1 \right) \quad (8)$$

where k, w1 and w2 are constant numbers.

9. The analyzing device according to claim 4,
wherein the processor calculates the index X by a following expression (9):

$$X = \frac{(A_1 - kA_2)^{w1}}{(kA_2)^{w2}} \quad (9)$$

where k, w1 and w2 are constant numbers.

10. The analyzing device according to claim 6,
wherein the constant number k is determined such that a value of the index X calculated based on the first image data $G_1$ and the second image data $G_2$ obtained by capturing a biological tissue whose molar ratio is known becomes closest to a theoretical value of the index X.

11. The analyzing device according to claim 10,
wherein, by obtaining measurement values of the indexes X of a plurality of different biological tissues whose molar ratios are known, the constant number k is determined such that a calibration curve representing a relationship between the known molar ratios and the measurement values of the indexes becomes closest to a reference line representing a relationship between the known molar ratios and theoretical values of the indexes X.

12. The analyzing device according to claim 6, wherein the constant number k is 1.

13. The analyzing device according to claim 4,
wherein:
the light source device comprises a third optical filter that selectively extracts, from the wide band light, light of a third illumination wavelength range in which a degree of absorption by the biological tissue is sufficiently lower than a degree of absorption in the first illumination wavelength range;
the image pick-up device generates third image data $R_3$ by capturing the biological tissue under illumination of the light of the third illumination wavelength range;
the processor is configured to calculate a first standardized reflectivity $SR_1$ by dividing the first image data $G_1$ by the third image data $R_3$ and calculates the absorption $A_1$ by one of following expressions (10) and (11):

$$A_1 = -\log SR_1 \quad (10)$$

$$A_1 = -SR_1 \quad (11); \text{ and}$$

the processor is configured to calculate a second standardized reflectivity $SR_2$ by dividing the second image data $G_2$ by the third image data $R_3$ and calculates the absorption $A_2$ by one of following expressions (12) and (13):

$$A_2 = -\log SR_2 \quad (12)$$

$$A_2 = -SR_2 \quad (13).$$

14. The analyzing device according to claim 13,
wherein:
the image pick-up device obtains first baseline image data $BL_1$ by capturing a colorless reference board under illumination of the light of the first illumination wavelength range, second baseline image data $BL_2$ by capturing the colorless reference board under illumination of the light of the second illumination wavelength range, and third baseline image data $BL_3$ by capturing the colorless reference board under illumination of the light of the third illumination wavelength range; and
the processor is configured to calculate the first standardized reflectivity $SR_1$ by a following expression (14), and calculates the second standardized reflectivity $SR_2$ by a following expression (15):

$$SR_1 = \frac{G_1/BL_1}{R_3/BL_3} \quad (14)$$

$$SR_2 = \frac{G_2/BL_2}{R_3/BL_3}. \quad (15)$$

15. The analyzing device according to claim 13,
wherein:
the image pick-up device is a color image pick-up device having an RGB color filter;
the third illumination wavelength range is a red color wavelength range; and
the third image data $R_3$ is image data obtained by a light-receiving element of the image pick-up device to which an R filter of the RGB color filter is attached.

16. The analyzing device according to claim 13,
wherein:
the image pick-up device is a color image pick-up device having an RGB color filter;
the image pick-up device obtains first baseline image data $BL_1$ by capturing a colorless reference board under illumination of the light of the first illumination wavelength band, second baseline image data $BL_2$ by capturing the colorless reference board under illumination of the light of the second illumination wavelength band, third baseline image data $BL_{3R}$, $BL_{3G}$ and $BL_{3B}$ of three primary colors by capturing the colorless reference board under illumination of the wide band light, and normal observation image data $R_N$, $G_N$ and $B_N$ of three primary colors by capturing the biological tissue under illumination of the wide band light; and
the processor is configured to calculate the first standardized reflectivity $SR_1$ by a following expression (16), and calculates the second standardized reflectivity $SR_2$ by a following expression (17):

$$SR_1 = \frac{G_1/BL_1}{\frac{R_N}{BL_{3R}} + \frac{G_N}{BL_{3G}} + \frac{B_N}{BL_{3B}}} \quad (16)$$

$$SR_2 = \frac{G_2/BL_2}{\frac{R_N}{BL_{3R}} + \frac{G_N}{BL_{3G}} + \frac{B_N}{BL_{3B}}}. \quad (17)$$

17. The analyzing device according to claim 1, further comprising a light reducer configured to reduce the light of the first illumination wavelength range such that exposure to obtain the first image data $G_1$ becomes substantially equal to exposure to obtain the second image data $G_2$.

18. The analyzing device according to claim 1, wherein the first biological substance is oxyhemoglobin, the second biological substance is deoxyhemoglobin, and the molar ratio is oxygen saturation.

19. The analyzing device according to claim 18,
wherein:
absorption by the first biological substance and the second biological substance corresponds to a Q-band of hemoglobin;
the image pick-up device has an RGB color filter; and
the first image data $G_1$ and the second image data $G_2$ are image data obtained by a light-receiving element of the image pick-up device to which a G filter of the RGB color filter is attached.

20. The analyzing device according to claim 1,
wherein the processor is configured to generate a distribution image representing distribution of the molar ratio between the first biological substance and the second biological substance in the biological tissue based on the index X.

21. The analyzing device according to claim 3, wherein:

the wide band light is white light;

the image pick-up device obtains normal image data by capturing the biological tissue under illumination of the white light; and the processor is configured to:

calculate an index Y representing a total hemoglobin amount based on the first image data $G_1$;

extract, as a lesion portion, a pixel having the index Y larger than a first reference value and having the index X smaller than a second reference value; and generate a lesion region highlighting image in which the pixel corresponding to the lesion region of the normal observation image data is highlighted.

22. The analyzing device according to claim 1, further comprising an endoscope having a tip portion in which the image pick-up device is provided.

23. An analyzing method implemented on an analyzing device, comprising:

obtaining first image data $G_1$ by capturing a biological tissue under illumination of light of a first illumination wavelength range which a first biological substance and a second biological substance contained in the biological tissue absorb;

obtaining second image data $G_2$ by capturing the biological tissue under illumination of light of a second illumination wavelength range lying within the first illumination wavelength range; and calculating an index X representing a molar ratio between the first biological substance and the second biological substance contained in the biological tissue based on the first image data $G_1$ and the second image data $G_2$, wherein the first illumination wavelength range includes both of an absorption peak wavelength of the first biological substance and an absorption peak wavelength of the second biological substance; and the second illumination wavelength range includes an absorption peak wavelength of one of the first biological substance and the second biological substance.

\* \* \* \* \*